United States Patent [19]

Telling et al.

[11] 4,203,801

[45] May 20, 1980

[54] CELL AND VIRUS CULTURE SYSTEMS

[75] Inventors: Ronald C. Telling, Woking; Roy J. Passingham, Fleet; Brian L. Kitchener; David G. Hopkinson, both of Farnborough, all of England

[73] Assignee: Burroughs Wellcome Co., Research Triangle Park, N.C.

[21] Appl. No.: 783,660

[22] Filed: Apr. 1, 1977

Related U.S. Application Data

[63] Continuation-in-part of Ser. No. 670,448, Mar. 25, 1976, Pat. No. 4,085,203, and Ser. No. 354,195, Apr. 25, 1973, abandoned.

[30] Foreign Application Priority Data

Apr. 26, 1972 [GB] United Kingdom ............... 19387/72

[51] Int. Cl.² .......................... C12K 9/00; C12B 3/00; C12K 5/00
[52] U.S. Cl. .................................................. 435/284
[58] Field of Search ................................ 195/1.8, 1.7

[56] References Cited

U.S. PATENT DOCUMENTS

| | | | |
|---|---|---|---|
| 3,493,651 | 2/1970 | Sloane | 195/1.1 |
| 3,717,551 | 2/1973 | Bizzini et al. | 195/1.1 |
| 4,055,466 | 10/1977 | Torney et al. | 195/1.8 |

FOREIGN PATENT DOCUMENTS

| | | |
|---|---|---|
| 1517758 | 1/1970 | Fed. Rep. of Germany . |
| 1598245 | 8/1970 | France . |
| 786824 | 11/1957 | United Kingdom . |
| 989247 | 4/1965 | United Kingdom . |

*Primary Examiner*—Shep K. Rose
*Attorney, Agent, or Firm*—Donald Brown

[57] ABSTRACT

A cell culture system which comprises living eucaryotic cells, such as those of human or animal origin, or mycophyta dispersed within a solid carrier body or bed, which carrier consists of porous or particulate material capable of retaining the cells while allowing liquid media to pass through or to have contact with the said cells, and processes for preparing and maintaining such culture systems, particularly for the purpose of virus propagation.

21 Claims, 1 Drawing Figure

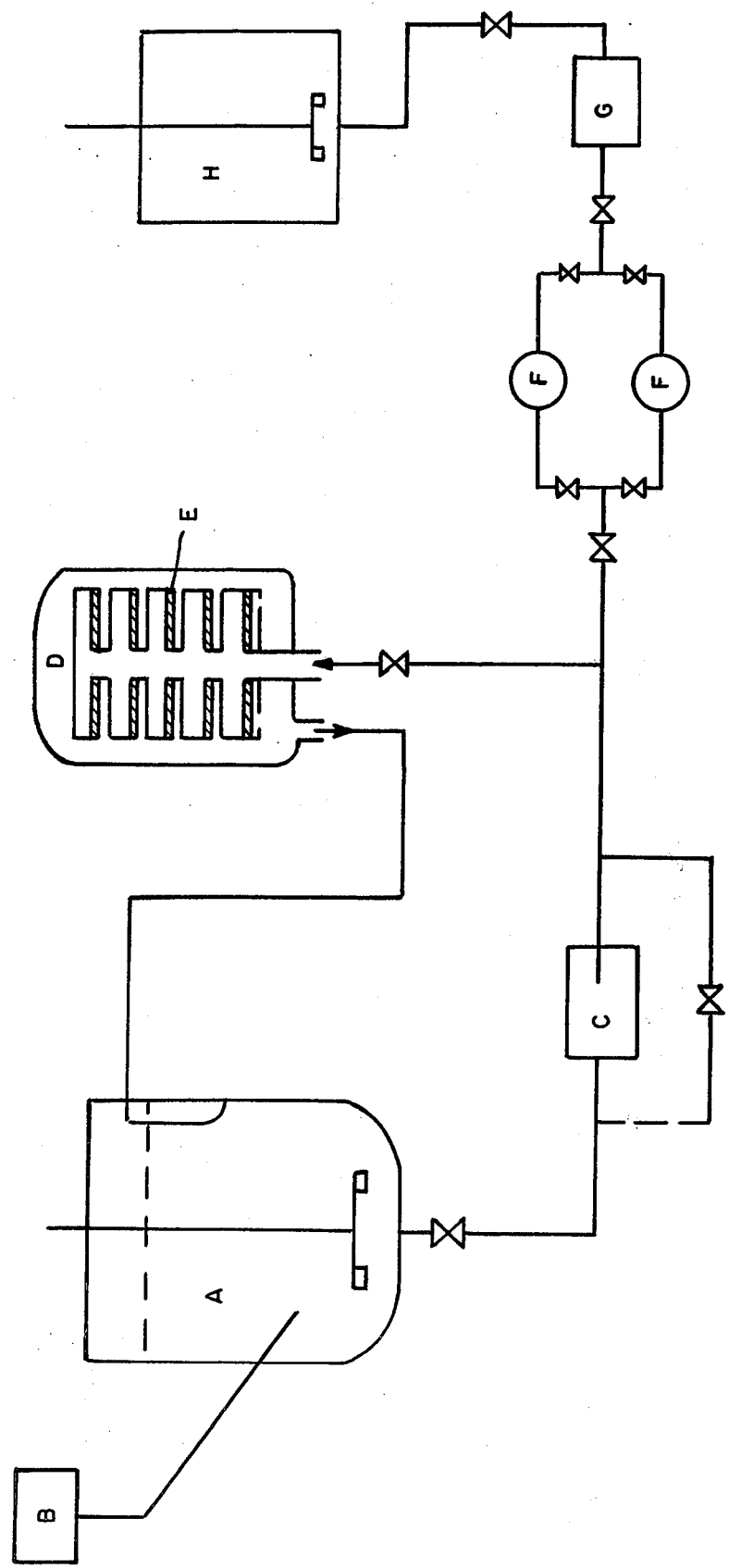

CELL AND VIRUS CULTURE SYSTEMS

This application is a continuation in part of Ser. No. 670,448, filed Mar. 25, 1976 now U.S. Pat. No. 4,085,203 and Ser. No. 354,195, filed Apr. 25, 1973, now abandoned.

This invention relates to the propagation of eucaryotic cells in a culture system and to the growth of microorganisms such as viruses in mammalian and human cells.

It is known that a variety of cell cultures, especially those of animal or human origin, can be maintained as monolayers on the smooth surface of a solid support, e.g. Petri-dishes, glass bottles, or tubes. As soon as such cultures become 'confluent', i.e. from a united layer of uniform thickness, a virus may be introduced in the liquid medium covering the cells, and the culture can be used for the propagation of the viruses in the monolayer system. Many types of cells can additionally be grown with advantage in suspension, i.e. substantial dispersion within the nutrient medium, and the same technique may also be adapted to the propagation of viruses in suspended cells. Apparatus for the purpose usually comprises a closed vessel or tank with appropriate means for agitation, control of environmental factors, e.g. pH, $pO_2$, supply of nutrients. (cf. B.P.S.1 090 758)

In the system conventionally used, for instance for growing cell lines in suspension culture, the cells are maintained in a submerged, stirred state in the medium and are sedimented by gravity when the peak concentration has been reached. The medium is then decanted off and the cells resuspended in a fresh medium which may also carry a virus seed. After the period of virus growth, as determined by observations of the cytopathic effect of the cells, the harvest is usually passed through a filter and then through a bacterial sterilising membrane to obtain a solution which contains free viruses released by the disrupted cells.

One difficulty with large scale suspended cultures of mammalian cells is that the sparging of air through the medium at a high rate may damage the cells, although a certain amount of oxygen supply is continuously required for optimum growth. Further difficulties are that the sedimentation of the cells is a time-consuming process (about 24 hours), the sedimented cells may be subjected to a medium environment unfavourable in terms of pH and nutritional factors, and only 95% of the used medium can be drained off without the risk of losing a substantial amount of the cells. Moreover, during the filtration of the virus harvest, the associated cell debris exerts a binding effect on the filter medium and, in order to achieve sterilising grade filtration, the ratio of volume filtered/filtration area must be low. This can cause serious losses (up to 50%) of viral antigen due to adsorption of virus on both the filter medium, particularly if this contains asbestos, and the retained cellular debris. Furthermore, the large vertical plate filter press required to provide an adequate filtration and usually gives rise to significant volume losses and, not being a sealed system, the consequent drips contitute a serious disease security hazard.

One object of the present invention is therefore to provide a system whereby the above disadvantages can be substantially overcome. Preferably the system should be applicable to cells of both the monolayer and suspension types and adapted to growth of viruses for the commercial production of vaccines.

It has now been found that cells can be grown with advantage within a solid carrier body or bed, which is either porous or is in a particulate state to provide sufficient internal cavities or space for immobilising and growing the cells and to allow liquid media to pass through the solid carrier and interact with the cells.

According to the present invention in one aspect, therefore, there is provided a cell culture system which comprises living eucaryotic cells of human or animal origin, or mycophyta, dispersed within a porous carrier body or bed, which carrier consists of particulate material which provides sufficient internal cavities or spaces for retaining and permitting the cells to grow and multiply within the bed, whilst allowing liquid media to pass through the carrier body or bed and to have contact with said cells. Eucaryotic cells refers to cells having a true nucleus containing chromosomes enclosed within a membrane, which chromosomes are capable of division by mitosis or meiosis.

The carrier may conveniently be provided in the form of a filter bed, and may consist of natural or synthetic materials, eg. silicates of the diatomaceous earth type, glass, or polymer particles. For instance various filter aids of diatomaceous earth such as kieselguhr, infusorial earth and in particular diatomite, may be convenient for the purpose. Other materials which may be used include spun glass, cellulosic pads, nylon or polystyrene beads. All these materials are virtually insoluble and biologically substantially inert.

The size of the pores, or the space available for cell growth within a bed of particulate materials can be suitably chosen and adjusted to requirements. It is often advantageous to select a 'retention size', indicating the filtering capability of the material which would effectively retain the cells but allow quick through-flow rates for liquids. Thus, conveniently, diatomaceous earths with reputed particle retention characteristics of 0.1 $\mu$m to 2.00 $\mu$m, preferably between 0.2 $\mu$m and 1.2 $\mu$m, eg. around 0.4 $\mu$m to 0.6 $\mu$m, may be used. The materials are suitably processed to remove impurities and sources of infection, and are graded and fractionated according to their particle size and other requirements.

More than one type of carrier material may be used to build up a suitable carrier for the cell. Thus a multibed system can be advantageous to increase the particle retention, and may for instance comprise consecutive layers of material with 0.5, 0.2, 0.5 and 1.2 $\mu$m reputed retention sizes from the basic perforated supporting plate or filter to the top. If a single layer is used this may still have to be provided with an additional top layer of low retention size, eg. 0.2 $\mu$m, immediately preceding the final filtration to increase the retention of smaller particles.

Any type of cell which is suitable for growth either in monolayers or in suspension can be incorporated in the culture system according to the present invention. The cell types in this respect include primary and secondary cell cultures, and diploid and heteroploid cell lines or strains of mammalian or human origin. For instance, the well-known IBRS2 pig kidney cell line or the baby hamster kidney cell line clone 21 (BHK21) are particularly suitable for the purpose. In cases of cells which can only be grown and used in monolayers, the culture system is eminently suitable for all stages of growth and also for the subsequent propagation of microorganism, such as viruses. Other cells which can efficiently be propagated in suspension cultures may first be processed in that manner and then incorporated in the culture system according to the invention for the purpose of virus propagation and harvest. In a particular aspect therefore the hereinbefore defined culture system also comprises cells infected with microorganisms, such as viruses to which the cells are susceptible. Of course, other types of eucaryotics, e.g. mycophyta such as yeasts, may also be applied to the carrier according to the present invention in an appropriate nutrient medium.

Standard horizontal pressure filters may, for instance, be used to support the culture system, but it is convenient to use a Calmic high duty horizontal plate pressure filter, such as the Calmic 45-S-9 E-type filter, as manufactured by Calmic Engineering Ltd., Crewe. Such a filter comprises nine horizontal plate units each of 45 cm diameter, having a total filtration area of 1.26 $m^2$. Each plate unit comprises a stainless steel perforated plate seated on a stainless steel dimpled plate. In use, a support sheet, e.g. of paper or rayon, may be employed on the perforated plate to support the filter bed.

In the preparation of the culture bed, slurries of the appropriate grades of the carrier material may be pumped in sequence from a convenient vessel through the plate filter whereby the carrier is retained on the plate. For each layer the slurry is recirculated several times until the filtrate is clear, leaving the required thickness of carrier bed on the support sheet or previous layer, which may be for instance about 8 mm to 20 mm, preferably 10 mm to 14 mm, most preferably 12 mm.

It is usual for a single layer to consist of material having a relatively large reputed particle retention size, e.g. 0.75 to 2.0 $\mu$m, preferably 1.2 $\mu$m, and, in the case of a multi-bed system, for the subsequent layers to be of relatively small particle retention size, e.g. 0.1 to 0.75, conveniently 0.2 to 0.5 $\mu$m.

The culture vessel may be of the conventional type, fitted with an agitator and means for measuring and controlling the pH, temperature, and for introducing air or oxygen to aerate the medium. It may further be supplied with an oxygen electrode which measures the dissolved oxygen tension in the culture medium and hence can be used as hereinafter described to determine the duration of the virus growth period.

Any culture media known to be suitable for the growth of the cells and/or of the microorganisms e.g. viruses associated with the cells, may be used, such as Eagles Basal Medium (*Science*, 122, 501 (1955)) or modified Eagles Medium (*Virology*, 16, 147 (1962). The media may also contain for instance 10% v/v bovine serum for the growth of BHK21 suspension cell line, and a reduced amount of serum, for instance 1% serum, for the growth of foot- and -mouth disease virus on this cell line.

Foot-and-mouth disease (hereinafter referred to as FMD) is caused by a variety of antigenically different virus types, several of which may be found in particular territories. For example, types O, A and C occur in Europe and South America, types SAT1, SAT2 and SAT3 occur in South Africa and types O, A, Asia I and SAT1 occur in the Near East. The following strains of FMD/virus have so far been found suitable for growth according to the present invention, namely A Pando, O BFS 1860, SAT1 Rho-5/66, SAT2 Swz.1/69 and SAT3 Bec 1/65.

The invention may be practised in two ways depending on whether the cell system has normally been grown in suspension or monolayer culture. In the former case the cells are propagated in submerged culture in a stirred vessel in the conventional way, and filtered through and retained on the bed when the cells have reached their maximum concentration. Cells only suitable for monolayer culturing may, on the other hand, be propagated with advantage within the culture system. Thus in the latter case the appropriate growth medium in the culture vessel may be inoculated with a cell seed and then immediately circulated through the previously prepared carrier bed, whereupon the cells are embedded and immobilised within the bed. The culture medium is then continuously circulated throughout the cell growth period. In both types of cases, medium suitable for virus growth may subsequently be added to the culture vessel, and the cells inoculated with the virus. The medium is again continuously circulated through the bed so that the virus may be propagated in the cells embedded within the carrier bed. As soon as the virus disrupts the cells the debris thereby formed remains within the carrier bed and the virus is released into the medium.

Although cell growth within the carrier bed cannot be directly observed, the growth may readily be monitored by glucose utilisation. The period of virus growth may be determined indirectly from readings of the oxygen electrode which gives the dissolved oxygen tension ($pO_2$) in the culture medium. Thus, in the early stages of the virus culture the oxygen uptake by the metabolising cells is in excess of the oxygen solution rate into the culture medium, and consequently the dissolved $pO_2$ falls. As cells die as the result of a virus infection there is a continually diminishing oxygen demand for cell metabolism which eventually is less than the oxygen solution rate so that the dissolved $pO_2$ rises. This change can therefore be used for the monitoring and control of the virus propagation stage and it has been found advantageous to harvest the virus culture when the dissolved $pO_2$ in the culture medium is in approximate equilibrium with the $pO_2$ value for conditions of air saturation.

The general sequence of operations in the practice of the present invention as exemplified by the cells capable of growing in suspension cultures is as follows. The cell culture is initiated in the stirred vessel in the normal way, the pH of the medium being about 7.4 and the temperature about 35° C. in most instances. A carrier bed is then prepared by pumping an aqueous slurry of the appropriate grades of carrier material, e.g. diatomaceous earth, in sequence, through an appropriate filter, preferably operating under pressure, and the system is sterilised and maintained in this state until required. When the cells have reached their maximum concentration the cell culture is passed through the bed at about 20 liters/minute flow rate, whereby the majority of the cells are immobilised in the carrier bed. The culture medium and any cells not so captured are pumped back into the culture vessel and recirculated through the filter until such time as less than 10% of the cells, preferably less than 5%, are found to be passing through the system. This may be determined indirectly by cell counts at intervals throughout the recirculation stage on samples taken from filtrate immediately leaving the filter. The filtrate is then pumped to waste, leaving the cells covered by the medium retained in the filter, however, until the virus growth stage is commenced.

For the purpose of virus growth a new medium usually with a different composition is introduced and passed through the cell culture system. An appropriate seed virus, to which the cells are susceptible, can then be introduced to infect the culture. After the cells are disrupted by the multiplied virus population, i.e. the cytopathic effect has taken place, a great number of virus is released and carried away by the medium.

The medium containing the virus particles separated from the cell debris in this manner can now be stored, or preferably subjected to filtration, removing any bacterial contamination from the medium. The viral antigen can then be inactivated with a suitable inactivating agent such as formaldehyde or especially acetylethyleneimine and formulated into a vaccine, which preferably incorporates an adjuvant such as aluminium hydroxide advantageously combined with saponin.

In another aspect therefore the invention provides a process for preparing and maintaining a cell culture system, as hereinbefore defined, which comprises the steps of (a) preparing a carrier bed from a slurry of porous or particulate material, (b) applying a liquid suspension of eucaryotic cells to the bed, (c) allowing the cells retained in the bed to establish themselves and (d) circulating nutrient medium through the bed, whereby nutrients are delivered to the cells and metabolic and degradation products are removed in the liquid leaving the bed.

In particular, the process also incorporates the additional steps of (e) infecting the cells with a microorganism to which the cells are susceptible, (f) culturing the microorganism in a nutrient medium, (g) separating the microorganism from the cell debris, and (h) if necessary removing bacterial contamination by filtration.

The process is specially suitable for growing viruses in cell lines, and may therefore be used with advantage to provide viral vaccines after appropriate inactivation if necessary.

In a further particular aspect the present invention provides a vaccine, which is prepared by a method incorporating the hereinbefore defined steps. Advantageously the virus used in the culture systems, methods, and vaccines, is an FMD virus.

The methods and systems recommended according to the present invention avoids the time-consuming sedimentation stage, in which the cells of the convential techniques are often kept in an unfavourable environment for prolonged periods. The removal of used cell medium can now be rapid and more or less complete. Furthermore, the change over from the cell culture medium to the virus growth medium can be easy and rapid, and should avoid the cross-contamination of the two media that often occurs with conventional system. The cells can conveniently be washed between stages if necessary. Since the cells and cellular debris remain trapped in the carrier bed, the pre-filtration, which is essential to get high through-puts through the final bacteriological sterilising filtration stage, is advantageously incorporated in the virus growth stage with a potential saving of several hours.

It is important that the desired nutrients may be added to recycling medium whenever required, and the medium can also be sparged with air at the maximum necessary rate, without risk of physical damage to cells. Moreover, the method can be operated in a closed system, which can for instance be sterilised for example by steam injection, and there is therefore no disease security hazard resulting from the drips and spills which occur with the conventional techniques.

The invention will now be more particularly described with reference to the FIGURE, which shows diagrammatically the interconnection of a pressure filter containing a carrier bed with a culture vessel and associated equipment.

In the FIGURE, a conventional culture vessel (A) is equipped with an electrode system (B) and media from the vessel may be pumped via pump (C) into a pressure filter (D) supporting a carrier bed (E). Cartridge filters (F) and membrane filters (G) serve to filter the virus harvest before it is passed into the inactivation tank (H).

EXAMPLE 1

Preparation of the Diatomaceous Earth Filter Beds

Filter beds used in the practice of the present invention were of three kinds (a) A single bed was prepared by pumping an aqueous slurry of 3000 g Dicalite 4200 of particle retention size 1.2 μm through the central orifice of the horizontal plates of a Calmic 45-S-9 pressure filter and down through each individual plate thereby leaving a layer of Dicalite on each plate. The filter system was then sterilised by steam injection. Immediately prior to the filtration of the virus harvest 1500 g of sterilised Superaid of reputed particle retention size 0.2 μm was added as body feed to the virus harvest.

(b) A single bed was prepared as under (a) by pumping 4000 g Dicalite through the pressure filter. 500 g of sterilised Superaid was added directly to the carrier bed immediately prior to the sterilising filtration.

(c) A multi-bed was prepared by pumping the following diatomaceous earths through the pressure filter in the order given: 1000 g Hyflo Supercel of reputed particle retention size 0.5 μm, 1000 g Superaid, 2000 g Hyflo Supercel and 1000 g Dicalite 4200, this system obviating the need for further additions of diatomaceous earths at the end of the virus cultivation stage.

The Calmic pressure filter was sterilised by steam injection at $1.37\times10^5$ Newton/meter$^2$ and held under positive pressure of sterile air until required. During use, the temperature of the filter was controlled by water circulating through the jacket of the filter.

EXAMPLE 2

Production of FMD Virus from BHK21 Suspension Cells Held in The Carrier Bed

A culture of 650 liters of a medium containing about $7\times10^5$/ml cloned baby hamster kidney cells (BHK21) was initiated in a sterile 700 liter closed culture vessel which was suitably equipped for pH control, for the addition of various nutrients during the cell culture and virus growth periods, and with an oxygen electrode to enable the dissolved oxygen tension ($pO_2$) to be determined.

The culture medium used was modified Eagles Medium (Virology 16, 147 (1962)) to which 10% v/v bovine serum was added. The temperature of the cell culture was maintained at 35° C. and kept there within ±0.25° C. and the rate of agitation by a reciprocating paddle was adjusted to 36 strokes/minute. An air flow was maintained at a rate of 5 l/min across the top of the medium and the pH adjusted to 7.4 and automatically maintained there within ±0.03 pH units by a flow of carbon dioxide gas at 10 l/min sparged through the medium or by the addition of 4 molar sodium hydroxide solution. An additional flow was automatically sparged through the culture medium at 15 l/min when readings given by the oxygen electrode indicated this was necessary.

The maximum concentration of the cells, about $2.5 \times 10^6$ cells/ml, was reached after 50 hours and the cell culture was then circulated at 20 l/min three times through the multi-bed filter prepared under Example 1 (c). Cell count determinations measured on samples taken from medium immediately leaving the filter at 15 minute intervals indicated that by this stage 96% of the cells at maximum concentration had been immobilised on the carrier bed. The spent, substantially cell-free medium was then pumped to waste leaving the carrier bed covered by the medium, however, until the virus cultivation stage.

650 liters of virus culture medium comprising modified Eagles Medium containing 1% v/v bovine serum was added to the culture vessel and brought to 35° C. The cell culture medium retained in the filter was drained to waste and circulation of the virus medium through the filter beds commenced. The medium in the culture vessel was then introduced with 2000 ml suspension of a strain of FMD virus designated Type A-Pando, which had been adapted to grow in BHK21 cells. The inoculated medium was recirculated through the filter for about 48 hours at a flow rate of 20 l/min, whereby the number of media changes in the filter was about 20/h and in the total culture volume about 2/h. The velocity with which the medium actually flowed through the carrier bed was about 1.8 cm/min. The pH of the medium was controlled at a pH value of 7.4 by the automatic injection of air and carbon dioxide gas through the medium.

The virus was propagated in the cells immobilised in the carrier bed to a titre of $10^{7.5}$ plaque forming units (pfu)/ml of culture fluid, samples for plaque assay being taken from the culture vessel at regular intervals during the day. The maximum complement fixation titre was 1/12.

The end of the virus culture period was determined by monitoring the $pO_2$ in the culture medium, and the culture was harvested when the $pO_2$ value had increased to a value equal to conditions of air saturation. The medium in the filter was then returned to the culture vessel by air pressure and the filter isolated from the system. The virus harvest in the medium was pumped through a two-stage bacterial, sterilising grade filtration system, which had been sterilised previously by steam injection.

In the first stage, the virus culture medium was adjusted to a pH of 7.6 with 2 molar glycine buffer and then filtered at room temperature and at a flow rate of 6.8 l/min through two Balston cartridge depth filters (47.5 cm $\times$ 3 cm) of bonded glass fibres. The filter cartridges, having a reputed particle retention size of 0.35 $\mu$m, were arranged in parallel to provide a filtration area of 1500 cm$^2$. In the second stage, the medium leaving the cartridge filters was pumped at the same rate at a pressure of $4.8-6.2 \times 10^4$ N/m through 20 Schleicher and Schüll membrane filters (20 cm $\times$ 20 cm), having a reputed particle retention size of 0.22 $\mu$m. These provide an effective filtration area of 6500 cm$^2$, or approximately 100 ml filtrate/cm$^2$ filtration area.

The viral antigen thereby obtained was inactivated in the pre-sterilised inactivation vessel by treatment with acetylethyeneimine (AEI) and formulated into a vaccine containing 2 ml of inactivated virus filtrate, 25% by volume of 2% w/v aluminium hydroxide and 5 mg saponin per cattle vaccine dose. The vaccine was tested in cattle by challenging with live virus 21 days post-vaccination and gave a potency result of 29.7 $PD_{50}$/dose.

EXAMPLE 3

Production of FMD Virus from BHK21 Suspension Cells Held in The Carrier Bed

In accordance with the procedure of Example 2, the SAT.2Swz. 1/69 strain of FMD was cultivated, filtered, inactivated and formulated as a vaccine. When tested in cattle the vaccine had a potency value of 29.3 $PD_{50}$/dose as calculated from the level of the titres of the circulating antibody present in the cattle 21 days after vaccination.

EXAMPLE 4

The growth of virus by the methods described using both single and multi-bed techniques was examined using a variety of FMD strains. The following table shows examples of the infectivity and the maximum complement fixation values obtained with the different strains employed:

| Scale (liters) | Diatomite Bed | Virus Strain | Infectivity ($log_{10}pfu$/ml) | Complement Fixation (cfu/ml) |
|---|---|---|---|---|
| 30 | Single | SAT.1-Rho 5/66 | 6.7 | 1/16 |
| " | " | O-BFS 1860 | 6.8 | 1/16 |
| " | " | O-BFS 1860 | 6.4 | 1/12 |
| 650 | " | A Pando | 6.3 | 1/24 |
| " | " | A Pando | 6.8 | 1/12 |
| " | Multi | A Pando | 7.5 | 1/12 |
| " | " | A Pando | 7.3 | ⅛ |
| " | " | SAT.1-Rho 5/66 | 6.4 | 1/6 |
| " | " | SAT.1-Rho 5/66 | 7.0 | ⅛ |
| " | " | SAT.2-SWZ. 1/69 | 7.1 | 1/6 |
| " | " | SAT.2-SWZ. 1/69 | 6.1 | ⅛ |
| " | " | SAT.3-BEC. 1/65 | 7.2 | 1/5 |
| " | " | SAT.3-BEC. 1/65 | 6.8 | 1/6 |

EXAMPLE 5

Production of FMD Virus From IBRS 2 Pig Kidney Cell Line Held in The Carrier Bed The procedure of Examples 2 and 3 was repeated using however IBRS 2 cells to support a suitably adapted strain of FMD virus. A vaccine having a satisfactory potency value was obtained as tested by challenging cattle with live virus 21 days post-vaccination.

EXAMPLE 6

Growth of BHK21 Cells Within the Carrier Bed in The Filter 500 liters of cell culture medium comprising modified Eagles Medium containing 10% v/v bovine serum was added to a 700 liter culture vessel, the medium brought to 35° C. and then inoculated with a cell seed to give a starting concentration of about $7 \times 10^5$ cells/ml of cloned baby hamster kidney monolayer cells (BHK21). The inoculated culture, together with 2000 g of Dicalite 4200 of reputed particle retention size 1.2 $\mu$m, was immediately pumped through a sterilised filter bed, prepared according to Example 1(a) at a rate of 20 l/min so that practically all of the cells were deposited in the carrier bed, being interspersed with the layers of the diatomaceous earth. The cell culture medium was recirculated continuously for 48 hours and the cells were cultured within the carrier bed, during which time the amount of glucose dissimilated was 2 g/l. The medium was then pumped to waste and fresh virus medium and inoculum of the O-BFS 1860 strain of FMD virus was added in accordance with the procedure of Example 1.

The virus produced was filtered, inactivated and formulated as one component of a trivalent vaccine, which contained the equivalent of 2 ml of each of the inactivated virus antigens, 25% by volume of 2% w/v aluminium hydroxide and 5 mg saponin per cattle dose. The trivalent vaccine was tested in cattle by challenging with live virus 21 days post vaccination, and the potency of the O-BFS 1860 component, produced and described in this Example, was 15.3 $PD_{50}$/dose.

We claim:

1. A cell culture system which comprises living eucaryotic cells of human or animal origin, or mycophyta, dispersed within a porous carrier bed, said carrier bed comprising particulate material, and a support means for said carrier bed, said particulate material providing sufficient internal cavities or spaces for retaining and permitting said cells to grow and multiply within said carrier bed, and said support means allowing liquid media to pass through and out of said carrier bed and to have contact with said cells.

2. A cell culture system according to claim 1 wherein the particle retention size of said carrier bed is from 0.1 to 2.00 μm.

3. A cell culture system according to claim 1 wherein said particulate material is a diatomaceous earth.

4. A cell culture system according to claim 1 wherein said diatomaceous earth is selected from the class consisting of diatomite and kieselguhr.

5. A cell culture system according to claim 1 wherein said carrier bed comprises more than one horizontal layer of particulate material.

6. A cell culture system according to claim 5 wherein the particle retention size of said layers of particulate material generally decreases from the top surface layer to the layer adjacent the bottom surface layer.

7. A cell culture system according to claim 6 wherein the particle retention size of said layers is from 0.1 to 0.75 μm.

8. A cell culture system according to claim 6 wherein the particle retention size of said layers is from 0.2 to 0.5 μm.

9. A cell culture system according to claim 6 wherein said bottom surface layer is of greater particle retention size than the layer adjacent thereto.

10. A cell culture system according to claim 9 wherein the particle retention size of said bottom surface layer is about 0.5 μm.

11. A cell culture system according to claim 1 wherein said carrier bed comprises a single layer of particle retention size 0.75 μm to 2.0 μm.

12. A cell culture system according to claim 11 wherein the particle retention size is 1.2 μm.

13. A cell culture system according to claim 1 wherein the thickness of a layer of said carrier bed is from 8 mm to 20 mm.

14. A cell culture system according to claim 1 wherein said eucaryotic cells are selected from the class consisting of baby hamster clone 21 cell line and IB2 Renal Swine pig kidney cell line.

15. A cell culture system according to claim 1 wherein said cells are infected with a microorganism.

16. A cell culture system according to claim 15 wherein said microorganism is a virus.

17. A cell culture system according to claim 16 wherein said virus is a strain of foot-&-mouth disease virus.

18. A cell culture system according to claim 1 wherein said carrier bed is supported on a horizontal plate pressure filter.

19. A cell culture system according to claim 1 wherein said carrier bed is supported on a porous support means.

20. A cell culture system according to claim 1 wherein said carrier bed is supported on a support means having means for allowing said liquid media to pass through and out of said carrier bed.

21. A recirculating cell culture system which comprises living eucaryotic cells of human or animal origin, or mycophyta, dispersed within a porous carrier bed, said carrier bed comprising particulate material, said particulate material providing sufficient internal cavities or spaces for retaining and permitting said cells to grow and multiply within said carrier bed, a support means for said carrier bed, said support means allowing liquid media to pass through and out of said carrier bed and to have contact with said cells, and means for recirculating said liquid media through said carrier bed.

* * * * *